United States Patent
Myslinski

(10) Patent No.: US 10,124,005 B1
(45) Date of Patent: Nov. 13, 2018

(54) MULTISYMPTOM MIGRAINE COMBINATION MEDICATION

(71) Applicant: Lisa Josette Myslinski, Chicago, IL (US)

(72) Inventor: Lisa Josette Myslinski, Chicago, IL (US)

( * ) Notice: Subject to any disclaimer, the term of this patent is extended or adjusted under 35 U.S.C. 154(b) by 0 days.

(21) Appl. No.: 15/844,445

(22) Filed: Dec. 15, 2017

(51) Int. Cl.
*A61K 31/522* (2006.01)
*A61K 31/167* (2006.01)
*A61P 25/06* (2006.01)

(52) U.S. Cl.
CPC .......... *A61K 31/522* (2013.01); *A61K 31/167* (2013.01); *A61P 25/06* (2018.01)

(58) Field of Classification Search
CPC ............................ A61K 31/167; A61K 31/522
See application file for complete search history.

(56) References Cited

U.S. PATENT DOCUMENTS

| | | | | |
|---|---|---|---|---|
| 5,972,916 A | * | 10/1999 | Armellino | A61K 31/60 514/165 |
| 2002/0099060 A1 | * | 7/2002 | Imanzahrai | A61K 31/137 514/263.31 |
| 2007/0298096 A1 | * | 12/2007 | Liu | A61K 9/2009 424/451 |

OTHER PUBLICATIONS

Excedrin® Migraine Product Label (Accessed from https://www.accessdata.fda.gov/drugsatfda_docs/label/2014/020802Orig1s024lbl.pdf Feb. 15, 2018) Jul. 15, 2014, 23 pages (Year: 2014).*

Antivert® Product Label (Accessed from https://www.accessdata.fda.gov/drugsatfda_docs/label/2012/010721s058lbl.pdf on Feb. 15, 2018) Oct. 2012 , 4 pages (Year: 2012).*

Konkel, L. and Weatherspoon, D. (2017). *Migraine-Associated Vertigo and Nausea in Adults and Children.* [online] Healthline. Available at: https://www.healthline.com/health/migraine/severe-acute-migraines-vertigo-nausea [Accessed Mar. 12, 2018].

* cited by examiner

*Primary Examiner* — James D. Anderson

(57) ABSTRACT

Migraine is a multi-symptom disease involving pain; histamine triggers; and nausea with or without vomiting. Current over-the-counter medications focus only on treating pain. This invention involves treating other common triggers and symptoms as well as pain. Acetaminophen and caffeine are already being used but the addition of meclizine is what makes this medication my invention. The addition of meclizine covers the other symptoms that make migraine sufferers miserable which is nausea/vomiting and treats the possible histamine mediated trigger of migraines because it has antihistaminic properties. As a migraine sufferer myself, I experience all of these symptoms and would very much like to have everything I need to cover these debilitating symptoms in one medication hence my invention.

2 Claims, No Drawings

MULTISYMPTOM MIGRAINE COMBINATION MEDICATION

BACKGROUND OF THE INVENTION

In the United States, more than 37 million people suffer from migraines. Migraines are associated with decreased productivity and have a deleterious effect on quality of life. It is estimated that the total cost of lost productive time due to migraines is 19.6 billion. The World Health Organization ranks migraine as the 19$^{th}$ most common reason for disability.

Migraines are a multi-symptom condition. Besides pain, light sensitivity, sound sensitivity, nausea and vomiting are common symptoms associated with a migraine attack as well. The current over-the-counter medications available for migraine treatment only focus on one symptom—pain. My invention will treat more symptoms associated with migraine because migraine is a multifactorial disease.

Histamine has vasodilative effects which suggests it may be involved in the pathophysiology of migraine. Systemically given histamine may cause and aggravate headaches and/or migraines. Hence, antihistamines may be and have proven to be helpful in migraine treatment. Also, allergies which are histamine mediated have been suggested as a possible migraine trigger. Hence, antihistamines may be beneficial in this situation. Nausea with or without vomiting commonly accompany migraines. Current over-the-counter medications do not address this often-debilitating symptom.

BRIEF SUMMARY OF THE INVENTION

My invention will consist of three medications; acetaminophen and caffeine for pain; and meclizine to prevent nausea and vomiting and to help with the possible histamine trigger component especially in people with allergies. Many hospitals use a migraine cocktail containing an antihistamine which has been shown to help many migraine sufferers. Currently there are no over-the-counter migraine medications that treat all of these symptoms in one drug.

Some migraines may be triggered by allergies in which case loratadine would be helpful because allergies are histamine related. Caffeine has been shown to attenuate the pain-relieving effects of acetaminophen. Caffeine causes constriction of blood vessels in the brain which is necessary to alleviate pain associated with migraine. Acetaminophen is an analgesic or pain reliever. Meclizine has antihistaminic and anticholinergic properties which means that it can help with preventing histamine triggered migraines and the anticholinergic property helps prevent nausea and vomiting. The purpose of this combination migraine medication is to help prevent and treat the most common symptoms and triggers of migraines besides just treating the most common obvious symptom which is pain of course.

DETAILED DESCRIPTION OF THE INVENTION

This invention is different from the current over-the-counter medications that treat migraines in that it contains three medications with meclizine as the ingredient that actually makes this different from products currently available for consumers to buy for treating migraine. Meclizine has two properties that make it very useful in migraine sufferers; antihistaminic and anticholinergic properties. Histamines have been shown to initiate or trigger migraines thus, by blocking histamines we can help prevent them from acting as a trigger. The anticholinergic property as well as the fact that meclizine is a first-generation antihistamine is its' mechanism of action for preventing nausea and vomiting. Acetaminophen is an analgesic that provides pain relief. And caffeine provides pain relief by causing constriction of blood vessels in the brain and has been shown to attenuate the pain-relieving effects of acetaminophen when used together.

This invention will contain three different ingredients: (1) acetaminophen 250 mg, (2) caffeine 60 mg, and (3) meclizine 6.25 mg in each caplet or tablet. These strengths may vary slightly depending on the manufacturer. Patients will be instructed on maximum dosage (maximum number of caplets/tablets/day) allowed per day. The usual and most likely side effects of these medications are already well known in literature. This invention will be for people 12 years of age and older. Certain population groups such as people with asthma, heart disease, taking a diuretic, have stomach bleeding, liver or kidney disease will be advised to contact their doctor before using this medication. Avoid drinking alcohol with this medication and if you are allergic to any component in this medication then do not take it. Patients will also be instructed not to take any other medications that contain similar ingredients while taking this medication. Store at 20-25 degrees celcius (68-77 degrees farenheit) and avoid humidity. Keep out of reach of children and close cap tightly after each use.

This invention will also contain inactive ingredients such as fillers and other commonly used inactive ingredients in caplets and tablet manufacturing such as gelatin; hydroxypropyl cellulose; titanium dioxide; etc. The aforementioned list are just examples of inactive ingredients that may or may not be used and is not all inclusive. There are many inactive ingredients that are frequently used in caplet/tablet/capsule formulations and found commonly in literature about medication manufacturing.

The claimed invention is:

1. A combination migraine medication comprising 6.25 mg meclizine, 250 mg acetaminophen, and 60 mg caffeine.

2. A method of treating a migraine in a subject in need thereof, comprising administering to said subject the combination migraine medication according to claim 1.

* * * * *